(12) United States Patent
Saha et al.

(10) Patent No.: US 11,205,136 B2
(45) Date of Patent: Dec. 21, 2021

(54) PER-ARTICLE PERSONALIZED MODEL FEATURE TRANSFORMATION

(71) Applicant: Microsoft Technology Licensing, LLC, Redmond, WA (US)

(72) Inventors: Ankan Saha, San Francisco, CA (US); Ajith Muralidharan, Sunnyvale, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 1029 days.

(21) Appl. No.: 15/441,967

(22) Filed: Feb. 24, 2017

(65) Prior Publication Data

US 2018/0060739 A1 Mar. 1, 2018
US 2019/0213483 A9 Jul. 11, 2019

Related U.S. Application Data

(60) Provisional application No. 62/378,674, filed on Aug. 23, 2016.

(51) Int. Cl.

| | |
|---|---|
| *G06N 20/00* | (2019.01) |
| *G06F 16/248* | (2019.01) |
| *G06F 16/2458* | (2019.01) |
| *G06F 16/25* | (2019.01) |
| *G16H 70/60* | (2018.01) |

(Continued)

(52) U.S. Cl.
CPC .......... *G06N 20/00* (2019.01); *G06F 16/248* (2019.01); *G06F 16/2471* (2019.01); *G06F 16/256* (2019.01); *G06N 5/022* (2013.01); *G06N 5/04* (2013.01); *G06Q 50/01* (2013.01); *G16H 70/60* (2018.01); *G16H 80/00* (2018.01); *H04L 67/306* (2013.01); *G16H 10/60* (2018.01); *H04L 67/10* (2013.01); *H04L 67/42* (2013.01)

(58) Field of Classification Search
CPC .......... G06N 20/00; G06N 5/022; G06N 5/04; G16H 70/60; G16H 80/00; G06F 16/2471; G06F 16/256; G06F 16/248; G06Q 50/01; H04L 67/306
See application file for complete search history.

(56) References Cited

U.S. PATENT DOCUMENTS

| | | |
|---|---|---|
| 9,122,989 B1 | 9/2015 | Morris et al. |
| 2011/0022602 A1 | 1/2011 | Luo et al. |

(Continued)

OTHER PUBLICATIONS

"Final Office Action Issued in U.S. Appl. No. 15/442,069", dated Apr. 9, 2020, 12 Pages.

(Continued)

*Primary Examiner* — Alan Chen
(74) *Attorney, Agent, or Firm* — Schwegman Lundberg & Woessner, P.A.

(57) ABSTRACT

A system, a machine-readable storage medium storing instructions, and a computer-implemented method as described herein are directed to a Fast Ranker Engine that identifies global model features present in an article in a social network service. The Fast Ranker Engine assembles respective fixed vectors based on at least one member account feature and each coefficient that corresponds to a present global article feature of the global model. The Fast Ranker Engine generates a transformation feature(s) for a prediction model of the article based on the respective fixed vectors.

20 Claims, 7 Drawing Sheets

(51) Int. Cl.
*G06N 5/02* (2006.01)
*G06Q 50/00* (2012.01)
*G06N 5/04* (2006.01)
*H04L 29/08* (2006.01)
*G16H 80/00* (2018.01)
*G16H 10/60* (2018.01)
*H04L 29/06* (2006.01)

(56) References Cited

U.S. PATENT DOCUMENTS

| | | |
|---|---|---|
| 2011/0258256 A1 | 10/2011 | Huberman et al. |
| 2012/0023043 A1* | 1/2012 | Cetin .................... G06Q 30/02 706/12 |
| 2012/0259919 A1 | 10/2012 | Fan et al. |
| 2013/0073568 A1* | 3/2013 | Federov ............. G06Q 30/0269 707/749 |
| 2013/0170541 A1* | 7/2013 | Pace .................... H04N 19/149 375/240.02 |
| 2015/0081609 A1 | 3/2015 | Hande et al. |
| 2015/0242967 A1 | 8/2015 | Shsh |
| 2015/0317357 A1 | 11/2015 | Harmsen et al. |
| 2017/0061286 A1 | 3/2017 | Kumar et al. |
| 2018/0060756 A1 | 3/2018 | Saha et al. |
| 2019/0213501 A9 | 7/2019 | Saha et al. |

OTHER PUBLICATIONS

"Non Final Office Action Issued in U.S. Appl. No. 15/442,069", dated Oct. 31, 2019, 30 Pages.

Lee, et al., "Classification-Based Collaborative Filtering Using Market Basket Data", In Journal of Expert Systems with Applications, vol. 29, Issue 3, Oct. 2005, pp. 700-704.

Li, et al., "User Comments for News Recommendation in Forum-Based Social Media", In Journal of Information Sciences, vol. 180, Issue 24, Dec. 15, 2010, pp. 4929-4939.

"Non Final Office Action Issued in U.S. Appl. No. 15/442,069", dated Dec. 10, 2020, 11 Pages.

Park, et al., "Pairwise Preference Regression for Cold-start Recommendation", In Proceedings of the third ACM Conference on Recommender Systems, Oct. 2009, pp. 21-28.

"Final Office Action Issued in U.S. Appl. No. 15/442,069", dated Apr. 29, 2021, 12 Pages.

* cited by examiner

PER-ARTICLE PERSONALIZED MODEL FEATURE TRANSFORMATION

CROSS-REFERENCE TO RELATED APPLICATIONS

This application claims the benefit of priority to U.S. Provisional Patent Application entitled "PER-ARTICLE PERSONALIZED MODELS FOR RECOMMENDING CONTENT EMAIL DIGESTS WITH PERSONALIZED CANDIDATE ARTICLE POOLS" Ser. No. 62/378,674, filed Aug. 23, 2016, which is hereby incorporated herein by reference in its entirety.

This application is related to U.S. Patent Application entitled "PER-ARTICLE PERSONALIZED MODELS FOR RECOMMENDING CONTENT EMAIL DIGESTS WITH PERSONALIZED CANDIDATE ARTICLE POOLS", U.S. Ser. No. 15/442,069, which is hereby incorporated herein by reference in its entirety.

TECHNICAL FIELD

The subject matter disclosed herein generally relates to the technical field of special-purpose machines that facilitate determining relevance of content, including software-configured computerized variants of such special-purpose machines and improvements to such variants, and to the technologies by which such special-purpose machines become improved compared to other special-purpose machines that facilitate determining relevance of content.

BACKGROUND

A social networking service is a computer- or web-based application that enables users to establish links or connections with persons for the purpose of sharing information with one another. Some social networking services aim to enable friends and family to communicate with one another, while others are specifically directed to business users with a goal of enabling the sharing of business information. For purposes of the present disclosure, the terms "social network" and "social networking service" are used in a broad sense and are meant to encompass services aimed at connecting friends and family (often referred to simply as "social networks"), as well as services that are specifically directed to enabling business people to connect and share business information (also commonly referred to as "social networks" but sometimes referred to as "business networks").

With many social networking services, members are prompted to provide a variety of personal information, which may be displayed in a member's personal web page. Such information is commonly referred to as personal profile information, or simply "profile information", and when shown collectively, it is commonly referred to as a member's profile. For example, with some of the many social networking services in use today, the personal information that is commonly requested and displayed includes a member's age, gender, interests, contact information, home town, address, the name of the member's spouse and/or family members, and so forth. With certain social networking services, such as some business networking services, a member's personal information may include information commonly included in a professional resume or curriculum vitae, such as information about a person's education, employment history, skills, professional organizations, and so on. With some social networking services, a member's profile may be viewable to the public by default, or alternatively, the member may specify that only some portion of the profile is to be public by default. Accordingly, many social networking services serve as a sort of directory of people to be searched and browsed.

DESCRIPTION OF THE DRAWINGS

Some embodiments are illustrated by way of example and not limitation in the figures of the accompanying drawings in which.

DETAILED DESCRIPTION

Figure 1:
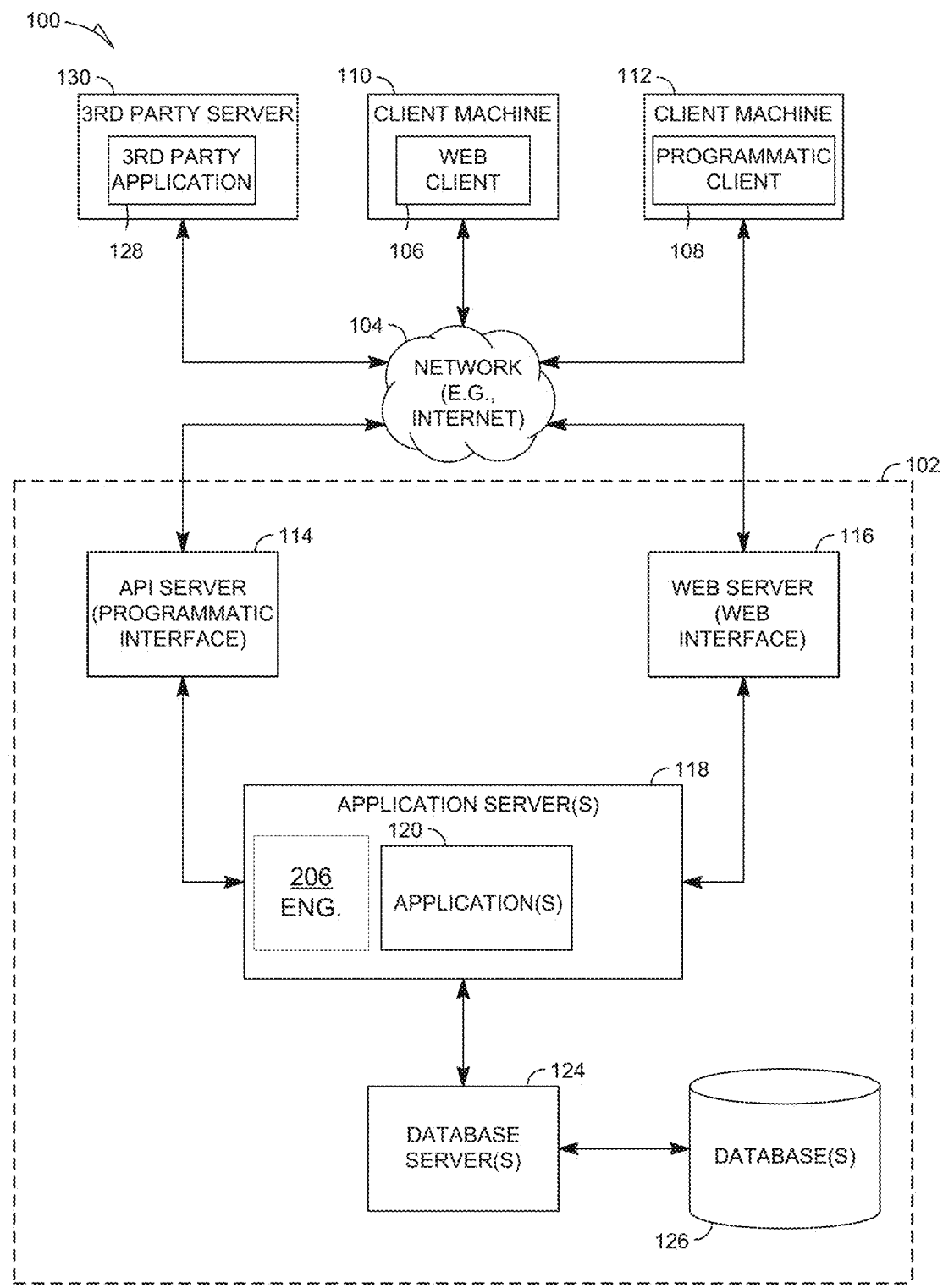
FIG. 1 is a block diagram illustrating a client-server system, in accordance with an example embodiment.

The present disclosure describes methods and systems for determining relevance of content in social network service (also referred to herein as a "professional social network" or "social network"). In the following description, for purposes of explanation, numerous specific details are set forth in order to provide a thorough understanding of the various aspects of different embodiments of the present invention. It will be evident, however, to one skilled in the art, that the present invention may be practiced without all of the specific details.

A system, a machine-readable storage medium storing instructions, and a computer-implemented method as described herein are directed to a Fast Ranker Engine that identifies global model features present in an article in a social network service. The Fast Ranker Engine assembles respective fixed vectors based on at least one member account feature and each coefficient that corresponds to a present global article feature of the global model. The Fast Ranker Engine generates a transformation feature(s) for a prediction model of the article based on the respective fixed vectors.

The Fast Ranker Engine improves the performance of a special-purpose computer system by more efficiently identifying relevant content in a social network system that may include millions of member accounts and millions of various types of content.

According to exemplary embodiments, a global model is trained and utilized to determine whether a given article is relevant to a member account in a social network service. The global model has a plurality of features with corresponding coefficients that can determine relevance of the given article to the target member account. The global model can be a logistic regression model that includes a plurality of global member features and a plurality of global article features (such as, for example, one or more keywords, topic, author, date of publication, associated member group, associated member discussion). In the global model, a feature vector is assembled based on any type(s) of present global model features in profile data of the target member account and social network data of the given article. In addition, a global vector is assembled based on global model coefficients that correspond to those present global model features. A global model score generated by the global model is based on a dot product of the feature vector and the global vector. The global model score represents a generalized score of the given article's relevance to the target member account.

In addition to the global model, each article in a plurality of candidate articles has its own prediction model. A prediction model has its own set of per-article features with corresponding coefficients, where the set of per-article features for the prediction model for a respective article are identified based on profile data of member accounts that have already interacted with the respective article. Each prediction model has its own set of coefficients that correspond with the per-article features of the prediction model. As such, a target member account vector can be assembled based on per-article features of the prediction model present in the profile data of the target member account and a prediction model vector is assembled based on prediction model coefficients that correspond to those present per-article features.

A prediction model score generated by the prediction model is based on a dot product of the target member account vector and the prediction model vector. The prediction model score represents a relevance score of the given article's relevance to the target member account. By combining an article's prediction model score with that article's global model score results in a highly particular evaluation of the article's relevance since prediction model features are based on other member accounts that have already determined that the respective article is worth accessing.

In one or more embodiments, the Fast Ranker Engine generates pre-computed transformation feature coefficients to be used in the global model to determine relevance between a given article and a target member account. Each member feature in the global model will have its own transformation coefficient for each article. That is, a first member feature in the global model will have a first transformation feature coefficient that corresponds with a first article, a second transformation feature coefficient that corresponds with a second article, a third transformation feature coefficient that corresponds with a third article, etc. As such, if there are 100 member features in the global model and there are 20 articles, each member feature with have 20 respective transformation features. Each transformation feature coefficient is pre-computed, reusable data that implicitly accounts for co-occurring article features in an article. Scoring by the global model is vastly improved by use of transformation features by eliminating the requirement of assembling vectors for article features.

According to various exemplary embodiments, the Fast Ranker Engine may be executed for the purposes of both off-line training for generating, training, and refining the global model and one or more of the prediction models.

Various example embodiments further include encoded instructions that comprise operations to generate a user interface(s) and various user interface elements. The user interface and the various user interface elements can be representative of any of the operations, data, prediction models, output, pre-defined features, identified features, coefficients, member accounts, notifications, profile data, articles, transformation features, fixed vectors, one or more type of member account interactions with articles, and scores as described herein. In addition, the user interface and various user interface elements are generated by the Fast Ranker Engine for display on a computing device, a server computing device, a mobile computing device, etc.

As described in various embodiments, the Fast Ranker Engine may be a configuration-driven system for building, training, and deploying prediction models for determining relevance of articles for a target member account. In particular, the operation of the Fast Ranker Engine is completely configurable and customizable by a user through a user-supplied configuration file such as a JavaScript Object Notation (JSON), eXtensible Markup Language (XML) file, etc.

For example, each module in the Fast Ranker Engine may have text associated with it in a configuration file(s) that describes how the module is configured, the inputs to the module, the operations to be performed by the module on the inputs, the outputs from the module, and so on. Accordingly, the user may rearrange the way these modules are connected together as well as the rules that the various modules use to perform various operations. Thus, whereas conventional prediction modelling is often performed in a fairly ad hoc and code driven manner, the modules of the Fast Ranker Engine may be configured in a modular and reusable fashion, to enable more efficient prediction modelling.

It is understood that, in various embodiments, the Fast Ranker Engine 206 generates the global model and each respective article prediction model by storing features and a coefficients in a data structure (in one or more databases) that represents the data model (such as a logistic regression model) of the global mode and/or each respective article prediction model. To execute the global model and a respective article prediction model, the Fast Ranker Engine 206 generates accesses an instruction set(s) that simulates data model calculations with respect to the features and the coefficients stored in the data structure and input as described herein.

Turning now to FIG. 1, FIG. 1 is a block diagram illustrating a client-server system, in accordance with an example embodiment. A networked system 102 provides server-side functionality via a network 104 (e.g., the Internet or Wide Area Network (WAN)) to one or more clients. FIG. 1 illustrates, for example, a web client 106 (e.g., a browser) and a programmatic client 108 executing on respective client machines 110 and 112.

An Application Program Interface (API) server 114 and a web server 116 are coupled to, and provide programmatic and web interfaces respectively to, one or more application servers 118. The application servers 118 host one or more applications 120. The application servers 118 are, in turn, shown to be coupled to one or more database servers 124 that facilitate access to one or more databases 126. While the applications 120 are shown in FIG. 1 to form part of the networked system 102, it will be appreciated that, in alternative embodiments, the applications 120 may form part of a service that is separate and distinct from the networked system 102.

Further, while the system 100 shown in FIG. 1 employs a client-server architecture, the present disclosure is of course not limited to such an architecture, and could equally well find application in a distributed, or peer-to-peer, architecture system, for example. The various applications 120 could also be implemented as standalone software programs, which do not necessarily have networking capabilities.

The web client 106 accesses the various applications 120 via the web interface supported by the web server 116. Similarly, the programmatic client 108 accesses the various services and functions provided by the applications 120 via the programmatic interface provided by the API server 114.

FIG. 1 also illustrates a third party application 128, executing on a third party server machine 130, as having programmatic access to the networked system 102 via the programmatic interface provided by the API server 114. For example, the third party application 128 may, utilizing information retrieved from the networked system 102, support one or more features or functions on a website hosted by the third party. The third party website may, for example, provide one or more functions that are supported by the relevant applications of the networked system 102. In some embodiments, the networked system 102 may comprise functional components of a professional social network.

Figure 2:
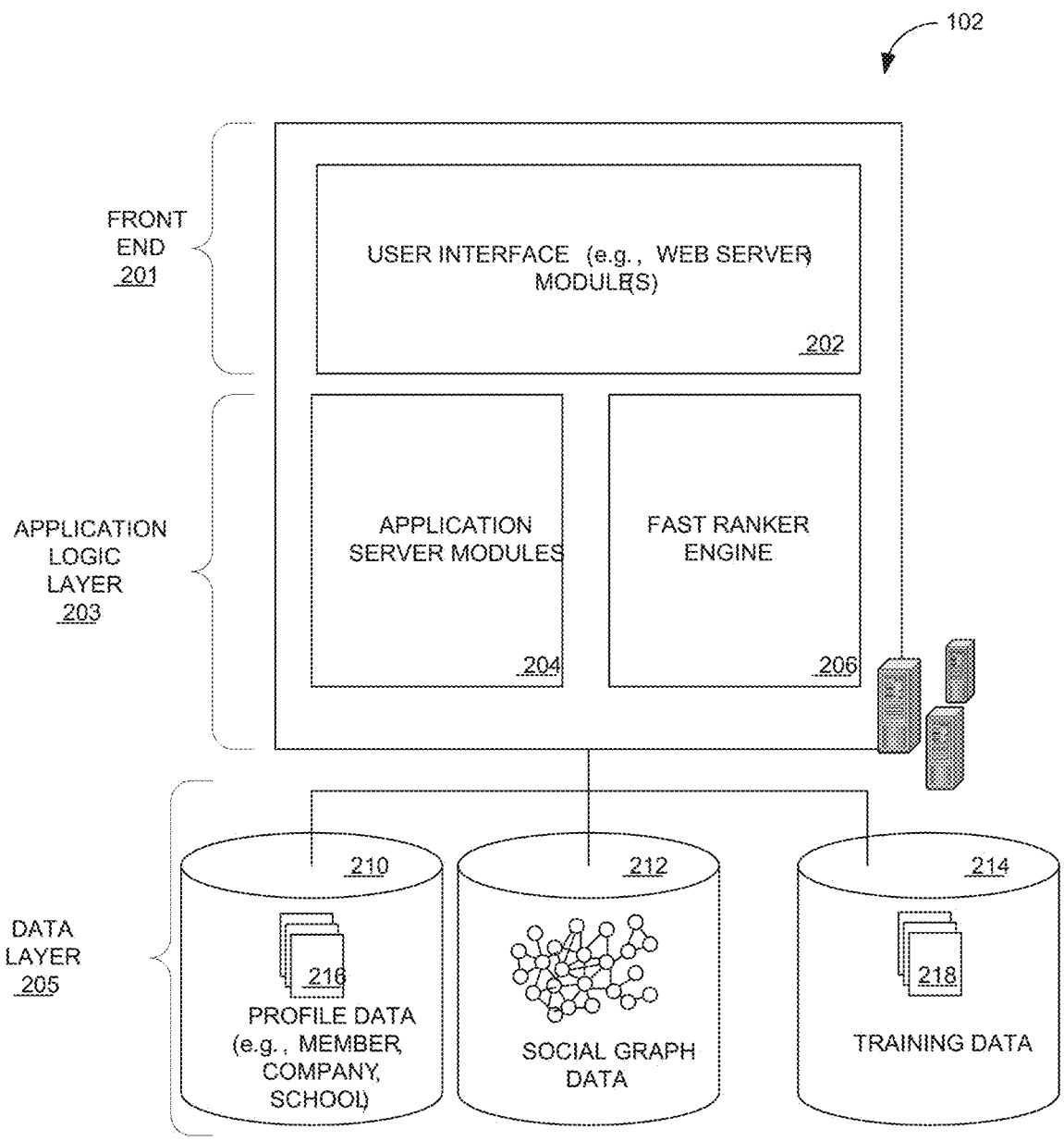
FIG. 2 is a block diagram showing functional components of a professional social network within a networked system, in accordance with an example embodiment.

FIG. 2 is a block diagram showing functional components of a professional social network within the networked system 102, in accordance with an example embodiment.

As shown in FIG. 2, the professional social network may be based on a three-tiered architecture, consisting of a front-end layer 201, an application logic layer 203, and a data layer 205. In some embodiments, the modules, systems, and/or engines shown in FIG. 2 represent a set of executable software instructions and the corresponding hardware (e.g., memory and processor) for executing the instructions. To avoid obscuring the inventive subject matter with unnecessary detail, various functional modules and engines that are not germane to conveying an understanding of the inventive subject matter have been omitted from FIG. 2. However, one skilled in the art will readily recognize that various additional functional modules and engines may be used with a professional social network, such as that illustrated in FIG. 2, to facilitate additional functionality that is not specifically described herein. Furthermore, the various functional modules and engines depicted in FIG. 2 may reside on a single server computer, or may be distributed across several server computers in various arrangements. Moreover, although a professional social network is depicted in FIG. 2 as a three-tiered architecture, the inventive subject matter is by no means limited to such architecture. It is contemplated that other types of architecture are within the scope of the present disclosure.

As shown in FIG. 2, in some embodiments, the front-end layer 201 comprises a user interface module (e.g., a web server) 202, which receives requests and inputs from various client-computing devices, and communicates appropriate responses to the requesting client devices. For example, the user interface module(s) 202 may receive requests in the form of Hypertext Transport Protocol (HTTP) requests, or other web-based, application programming interface (API) requests.

In some embodiments, the application logic layer 203 includes various application server modules 204, which, in conjunction with the user interface module(s) 202, generates various user interfaces (e.g., web pages) with data retrieved from various data sources in the data layer 205. In some embodiments, individual application server modules 204 are used to implement the functionality associated with various services and features of the professional social network. For instance, the ability of an organization to establish a presence in a social graph of the social network service, including the ability to establish a customized web page on behalf of an organization, and to publish messages or status updates on behalf of an organization, may be services implemented in independent application server modules 204. Similarly, a variety of other applications or services that are made available to members of the social network service may be embodied in their own application server modules 204.

As shown in FIG. 2, the data layer 205 may include several databases, such as a database 210 for storing profile data 216, including both member profile attribute data as well as profile attribute data for various organizations. Consistent with some embodiments, when a person initially registers to become a member of the professional social network, the person will be prompted to provide some profile attribute data such as, such as his or her name, age (e.g., birthdate), gender, interests, contact information, home town, address, the names of the member's spouse and/or family members, educational background (e.g., schools, majors, matriculation and/or graduation dates, etc.), employment history, skills, professional organizations, and so on. This information may be stored, for example, in the database 210. Similarly, when a representative of an organization initially registers the organization with the professional social network the representative may be prompted to provide certain information about the organization. This information may be stored, for example, in the database 210, or another database (not shown). With some embodiments, the profile data 216 may be processed (e.g., in the background or offline) to generate various derived profile data. For example, if a member has provided information about various job titles the member has held with the same company or different companies, and for how long, this information can be used to infer or derive a member profile attribute indicating the member's overall seniority level, or a seniority level within a particular company. With some embodiments, importing or otherwise accessing data from one or more externally hosted data sources may enhance profile data 216 for both members and organizations. For instance, with companies in particular, financial data may be imported from one or more external data sources, and made part of a company's profile.

The profile data 216 may also include information regarding settings for members of the professional social network. These settings may comprise various categories, including, but not limited to, privacy and communications. Each category may have its own set of settings that a member may control.

Once registered, a member may invite other members, or be invited by other members, to connect via the professional social network. A "connection" may require a bi-lateral agreement by the members, such that both members acknowledge the establishment of the connection. Similarly, with some embodiments, a member may elect to "follow" another member. In contrast to establishing a connection, the concept of "following" another member typically is a unilateral operation, and at least with some embodiments, does not require acknowledgement or approval by the member that is being followed. When one member follows another, the member who is following may receive status updates or other messages published by the member being followed, or relating to various activities undertaken by the member being followed. Similarly, when a member follows an organization, the member becomes eligible to receive messages or status updates published on behalf of the organization. For instance, messages or status updates published on behalf of an organization that a member is following will appear in the member's personalized data feed or content stream. In any case, the various associations and relationships that the members establish with other members, or with other entities and objects, may be stored and maintained as social graph data within a social graph database 212.

The professional social network may provide a broad range of other applications and services that allow members the opportunity to share and receive information, often customized to the interests of the member. For example, with some embodiments, the professional social network may include a photo sharing application that allows members to upload and share photos with other members. With some embodiments, members may be able to self-organize into groups, or interest groups, organized around a subject matter or topic of interest. With some embodiments, the professional social network may host various job listings providing details of job openings with various organizations.

In some embodiments, the professional social network provides an application programming interface (API) module via which third-party applications can access various services and data provided by the professional social network. For example, using an API, a third-party application may provide a user interface and logic that enables an authorized representative of an organization to publish messages from a third-party application to a content hosting platform of the professional social network that facilitates presentation of activity or content streams maintained and presented by the professional social network. Such third-party applications may be browser-based applications, or may be operating system-specific. In particular, some third-party applications may reside and execute on one or more mobile devices (e.g., a smartphone, or tablet computing devices) having a mobile operating system.

The data in the data layer 205 may be accessed, used, and adjusted by the Fast Ranker Engine 206 as will be described in more detail below in conjunction with FIGS. 3-7. Although the Fast Ranker Engine 206 is referred to herein as being used in the context of a professional social network, it is contemplated that it may also be employed in the context of any website or online services, including, but not limited to, content sharing sites (e.g., photo- or video-sharing sites) and any other online services that allow users to have a profile and present themselves or content to other users. Additionally, although features of the present disclosure are referred to herein as being used or presented in the context of a web page, it is contemplated that any user interface view (e.g., a user interface on a mobile device or on desktop software) is within the scope of the present disclosure.

The data layer 205 further includes a database 214 that includes training data 214 for generating the global model and one or more prediction models. The database 214 can further store the global model and one or more prediction models.

Figure 3:
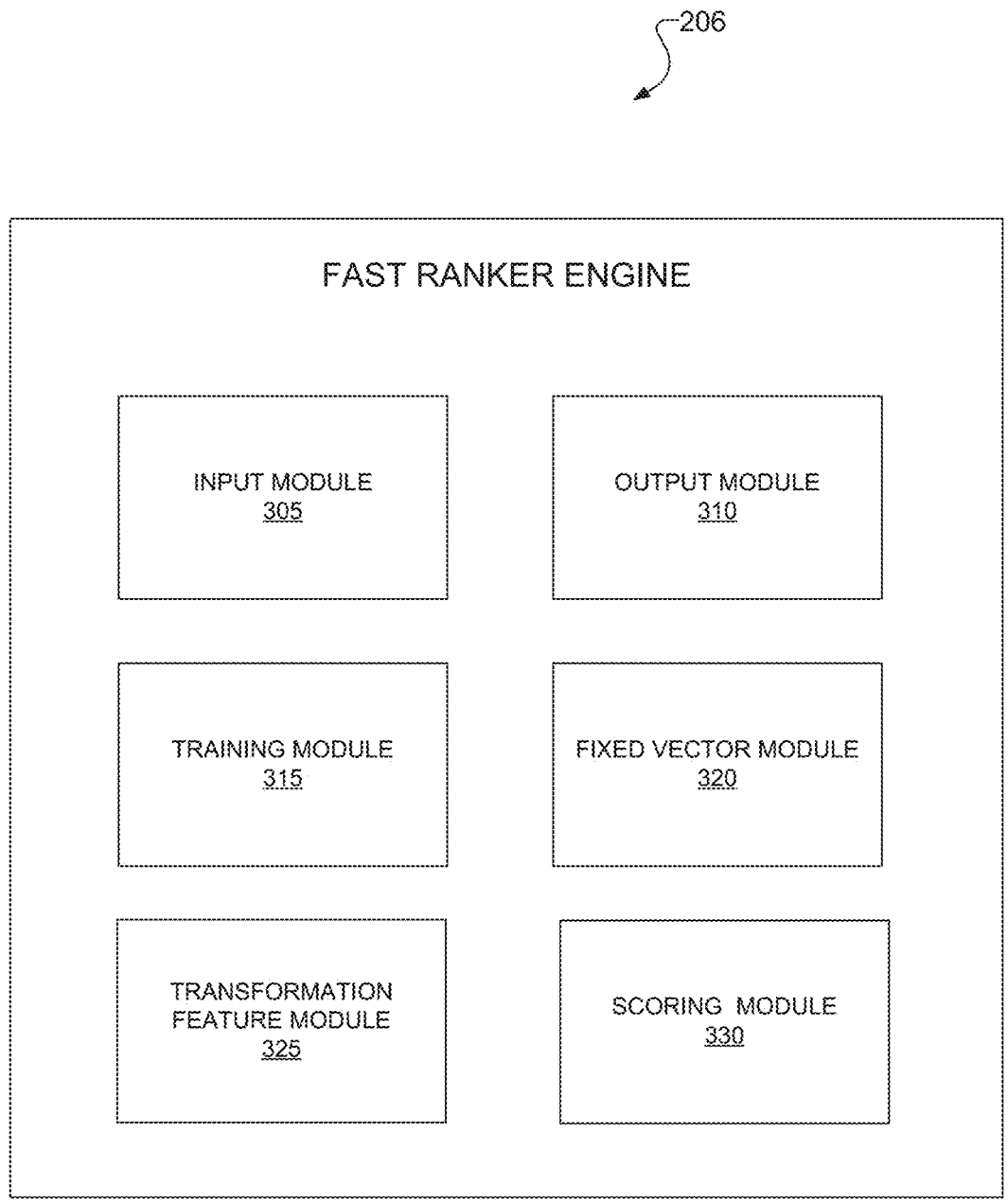
FIG. 3 is a block diagram showing example components of a Fast Ranker Engine, according to some embodiments.

FIG. 3 is a block diagram showing example components of a Fast Ranker Engine, according to some embodiments.

The input module 305 is a hardware-implemented module that controls, manages and stores information related to any inputs from one or more components of system 102 as illustrated in FIG. 1 and FIG. 2. In various embodiments, the inputs include, in part, one or more candidate articles, profile data of member accounts, social network data corresponding to the articles, and profile data of member account that have interacted with the one or more candidate articles. Input can also be the global model and one or more prediction models.

The output module 310 is a hardware-implemented module that controls, manages and stores information related to which sends any outputs to one or more components of system 100 of FIG. 1 (e.g., one or more client devices 110, 112, third party server 130, etc.). In some embodiments, the output is a message or notification that includes a digest (such as a listing) of one or more articles that have scores that indicate a relevance to the target member account.

The training module 315 is a hardware-implemented module which manages, controls, stores, and accesses information related to generating a global model and a prediction model for each article in a plurality of candidate articles.

The fixed vector module 320 is a hardware-implemented module which manages, controls, stores, and accesses information related to assembling fixed vectors as described herein.

The transformation feature module 325 is a hardware-implemented module which manages, controls, stores, and accesses information related to calculating dot product results between fixed vectors.

The scoring module 330 is a hardware-implemented module which manages, controls, stores, and accesses information related to ranking scores produced as output from the global mode and each prediction model for each article.

Figure 4:
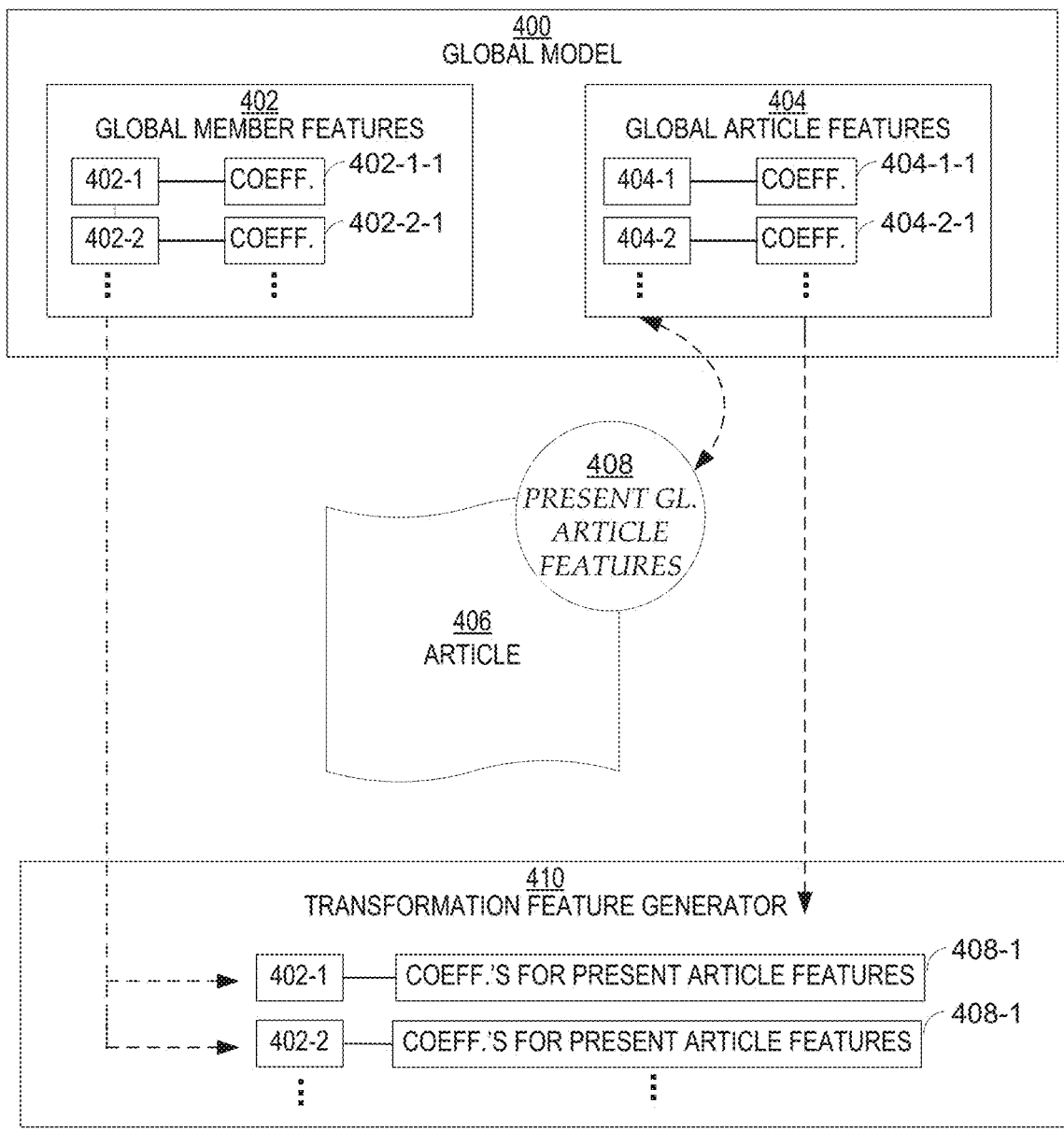
FIG. 4 is a block diagram showing example data flow of a Fast Ranker Engine, according to some embodiments.

FIG. 4 is a block diagram showing example data flow of a Fast Ranker Engine 206, according to some embodiments.

A global model 400 is trained, updated and utilized by the Fast Ranker Engine 206. The global model includes one or more global member features 402. Each global member feature is based on one or more types of attributes in profile data in member accounts. Such profile data can be, for example, descriptors of: any of a plurality of types of industry, any of a plurality of types of companies, any of a plurality of types of skills, any of a plurality of types of fields of study, any of a plurality of types of levels of professional experience, any of a plurality of types of schools, and/or any of a plurality of types of job titles. For example, a first global member feature 402-1 can be a first type of industry and a second global member feature 402-2 can be a second type of industry. Each global member feature 402-1, 402-2 has a corresponding coefficient 402-1-1, 402-2-1, such as a regression coefficient when the global model is a logistic regression model.

The global model 400 includes one or more global article features 404. Each global article feature is based on one or more types of attributes in article data in the social network service. Such article data can be, for example, one or more keywords, one or more topics, an article age, an article publishing date, one or more social network member groups in which the article is posted, one or more social network discussions regarding the article, etc. For example, a first global article feature 404-1 can be a first keyword and a second global article feature 404-2. can be a second keyword. Each global article feature 404-1, 404-2 has a corresponding coefficient 404-1-1, 404-2-1, such as a regression coefficient when the global model is a logistic regression model. Another present global model feature 408 present in the article 406 can also be the age of the article 406, which indicates how long the article 406 has been posted on the social network service. It is understood that there can be any number of global member features and global article features in the global mode 400—each feature having its own corresponding coefficient (such as, for example, a regression coefficient).

The Fast Ranker Engine 206 identifies global article features 408 present in an article 406 from a plurality of candidate articles. For example, the Fast Ranker Engine 206 detects that the 406 article contains at least one instance of the first keyword 404-1 and at least one instance of the second keyword 404-2. Based on presence of the keywords 404-1, 404-2 in the article 406, a transformation feature generator 401 of the Fast Ranker Engine 206 accesses the coefficients 404-1-1, 404-2-1 of the present global article features 408 and associates the coefficients 404-1-1, 404-2-1 with each global member feature 402-1, 402-2 of the global model 400. If, for example, the global model 400 has 100 global member features, the Fast Ranker Engine 206 associates each respective global member feature with the coefficients of the present global article features 408.

According to various exemplary embodiments, the training module 320 trains the global model 400 and a prediction model for each article in the plurality of candidate articles. To accomplish such training, the training module 320 may perform a prediction modelling process based on a statistics-based machine learning model such as a logistic regression model. As understood by those skilled in the art, logistic regression is an example of a statistics-based machine learning technique that uses a logistic function. The logistic function is based on a variable, referred to as a logit. The logit is defined in terms of a set of regression coefficients of corresponding independent predictor variables. Logistic regression can be used to predict the probability of occurrence of an event given a set of independent/predictor variables. The independent/predictor variables of the logistic regression model are the attributes represented by assembled feature vectors described throughout. The regression coefficients may be estimated using maximum likelihood or learned through a supervised learning technique from data collected (such as profile data and article data) in logs or calculated from log data, as described in more detail below. Accordingly, once the appropriate regression coefficients are determined, the features included in the assembled feature vector may be input to the logistic regression model in order to predict the probability that the event occurs (where the event Y may be, for example, whether a target member account would select to view a particular article).

In other words, provided an assembled feature vector including various features associated with a particular member account, a particular content item, a particular context, and so on, the assembled feature vector may be applied to a logistic regression model to determine the probability that the particular member account will respond to the particular content item in a particular way (e.g., click) given the particular context. Logistic regression is well understood by those skilled in the art, and will not be described in further detail herein, in order to avoid occluding various aspects of this disclosure.

It is understood that the training module 320 may use various other prediction modelling techniques understood by those skilled in the art to predict whether a particular member account will click on a particular content item in a particular context. For example, other prediction modelling techniques may include other machine learning models such as a Näive Bayes model, a support vector machines (SVM) model, a decision trees model, and a neural network model, all of which are understood by those skilled in the art. Also, according to various exemplary embodiments, the training module 320 may be used for the purposes of both off-line training (for generating, training, and refining a prediction model 412, 414, 416) and online inferences (for predicting whether a particular member will click on a particular content item given a particular context, based on a prediction model that corresponds with the particular content item).

Figure 5:
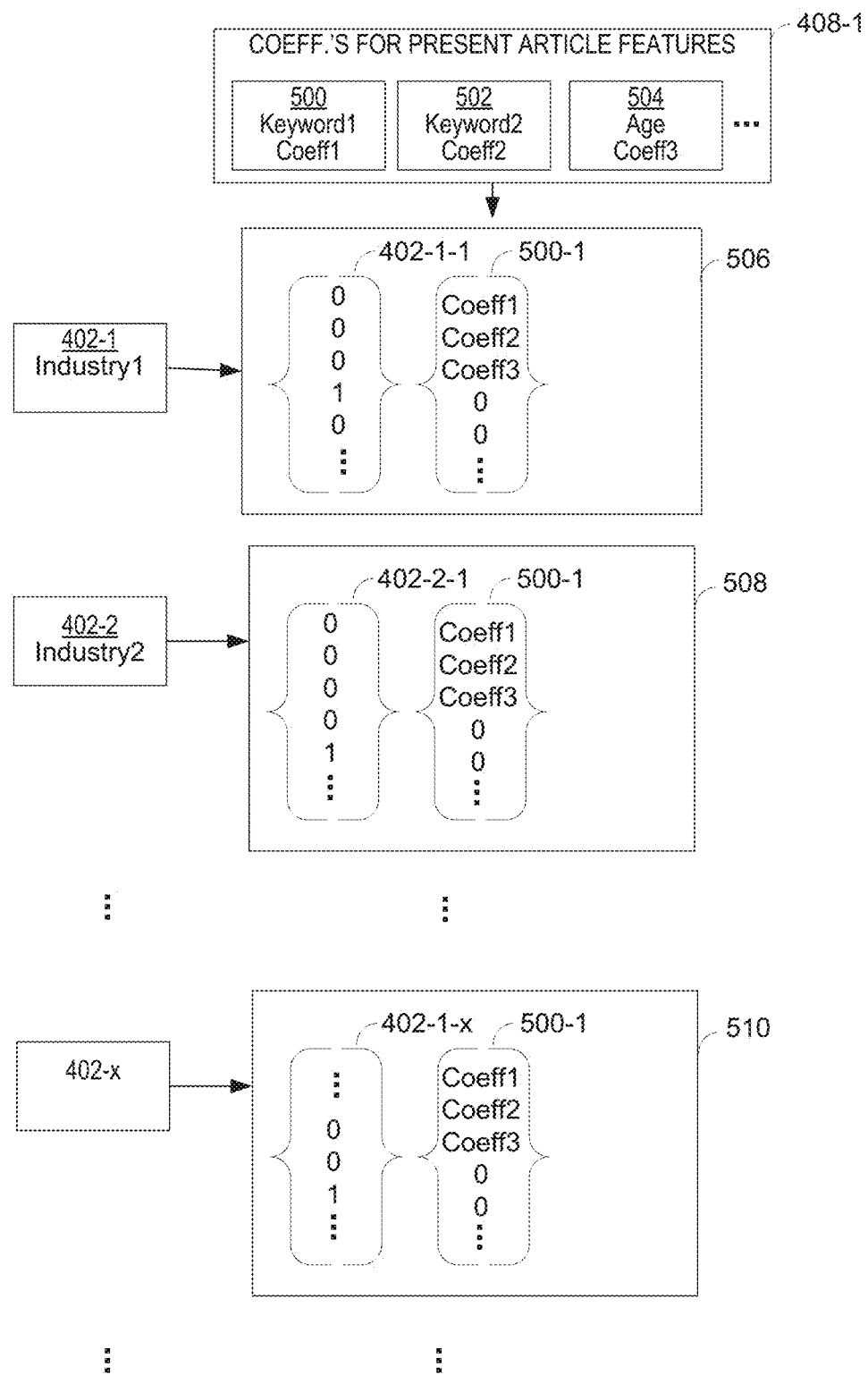
FIG. 5 is a block diagram showing example data flow of a Fast Ranker Engine, according to some embodiments.

FIG. 5 is a block diagram showing example data flow of a Fast Ranker Engine 206, according to some embodiments.

The transformation feature generator 410 of the Fast Ranker Engine 206 assembles a fixed member vector for each member feature in the global model 400. For example, the Fast Ranker Engine 206 assemble a first fixed member vector 402-1-1 that represents the first global member feature 402-1 ("Industry1") and a second fixed member vector 402-2-1 that represents the second global member feature 402-2 ("Industry2"). The first fixed member vector 402-1-1 includes only a "1" at a vector position assigned to the first global member feature 402-1. All other positions in the fixed member vector 402-1-1 are "0" (i.e. zero). The second fixed member vector 402-2-1 includes only a "1" at a vector position assigned to the second global member feature 402-2. All other positions in the fixed member vector 402-2-1 are "0" (i.e. zero). A fixed member vector 402-1-$x$ is similarly assembled for each member feature 402-$x$ in the global model 400

The transformation feature generator 410 assembles a fixed coefficient vectors 500-1 based on the coefficients 408-1 of global model article features 408 present in the article 406. For example, the transformation feature generator 410 assembles the fixed coefficient vector 500-1 based on the coefficients 500, 502, 504 for the first keyword feature ("Keyword1"), the second keyword feature ("Keyword2") and the age article feature ("Age").

The fixed coefficient vector 500-1 includes the coefficient 500 for the first keyword at a vector position assigned to the first keyword global article feature ("Keyword1"), the coefficient 502 for the second keyword at a vector position assigned to the second keyword global article feature ("Keyword2") and the coefficient 504 for the article age at a vector position assigned to the article age global article feature ("Age"). All other positions in the fixed coefficient vector 500-1 are "0" (i.e. zero).

The transformation feature generator 410 of the Fast Ranker Engine 206 calculates a first dot product 506 of the first fixed member vector 402-1-$i$ and the fixed coefficient vector 500-1, a second dot product 508 of the second fixed member vector 402-2-1 and the fixed coefficient vector 500-1 and a third dot product 510 of a respective fixed member vector 402-1-$x$ and the fixed coefficient vector 500-1. Again, it is understood that the Fast Ranker Engine 206 assembles a fixed member vector for each type of member feature from the global model 400. A dot product is calculated for each respective fixed member vector and the fixed coefficient vector 500-1.

The transformation feature generator 410 collects the first, second and third dot products 506, 508, 501 as transformation feature data for user by the global model 400. The transformation feature data includes a reusable, pre-computed coefficient value for each respective member feature of the global model 400.

Figure 6:
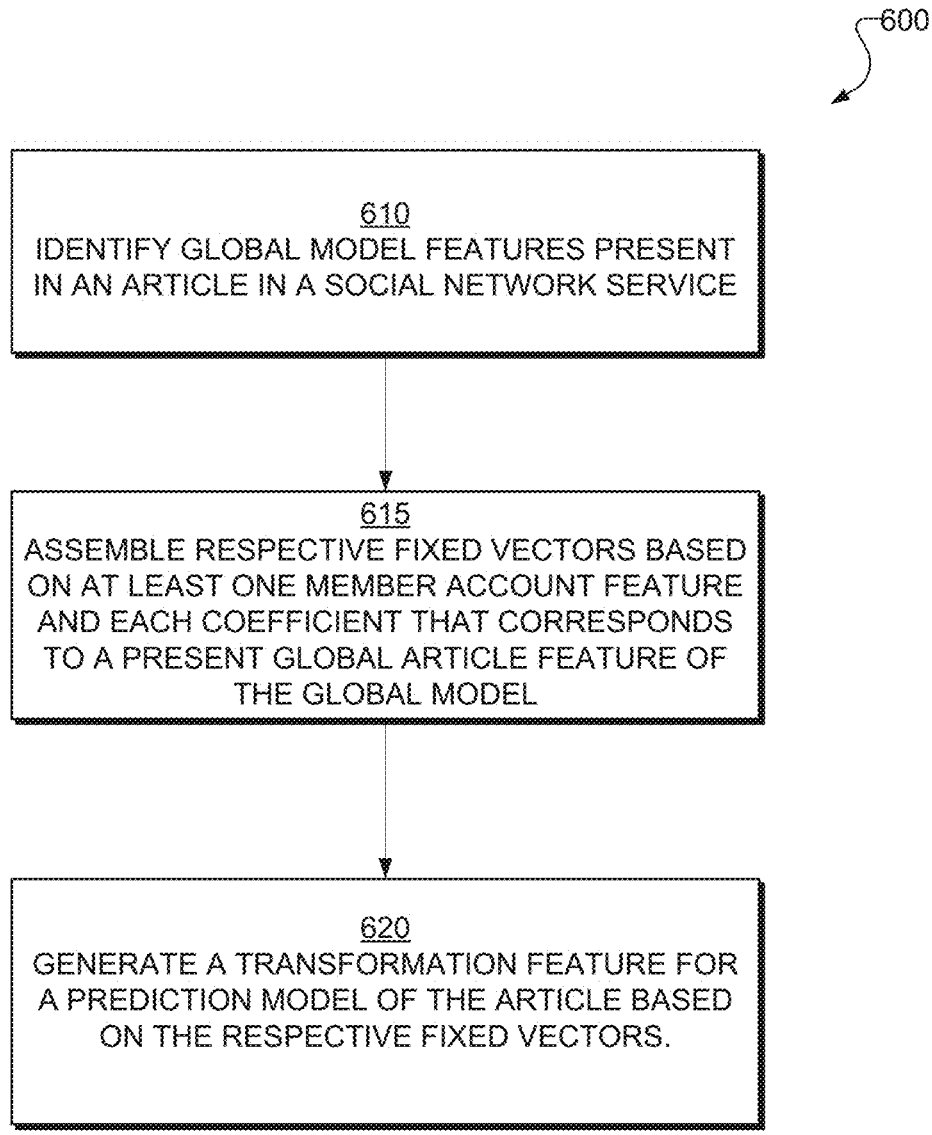
FIG. 6 is a flowchart illustrating an example method for according to an example embodiment.

FIG. 6 is a flowchart 600 illustrating an example method for . . . according to an example embodiment.

At operation 610, the Fast Ranker Engine 206 identifies global model features present in an article in a social network service.

According to an example that is simplified for explanation purposes, if there are three different types of global model member features ("mf1," "mf2," "mf3") and two different types of global model article features ("af1," "af2"), detected as being present in a respective article, the Fast Ranker Engine 206 computes a first transformation feature for "mf1" and a second transformation feature for "mf2."

At operation 615, the Fast Ranker Engine 206 assembles respective fixed vectors based on at least one member account feature and each coefficient that corresponds to a present global article feature of the global model.

A transformation feature is based on at least one fixed member feature and one or more article features present in a respective article. For example, to compute a first transformation feature for "mf1," the Fast Ranker Engine 206 assembles a first fixed member feature vector that represents presence of only the feature of "mf1", a second fixed member feature vector that represents presence of only the feature of "mf2" and assembles a fixed coefficient vector that includes the coefficients of all the present article features, such as a first coefficient for "af1" and a second coefficient for "af2".

At operation 620, the Fast Ranker Engine 206 generates a transformation feature for a prediction model of the article based on the respective fixed vectors.

The Fast Ranker Engine 206 computes a first transformation feature based on a first dot product score of the first fixed member feature vector and fixed coefficient vector and a second transformation feature based on a second dot product score of the second fixed member feature vector and the fixed coefficient vector.

The first transformation feature thereby represents a pre-computed coefficient that represents a relevance weight of the article for any member account that has the global member feature "mf1" that takes into account that the article features "af1," "af2" of the article will always be co-occurring with each other. The Fast Ranker Engine 206 stores the first transformation feature with an identifier associated with the "mf1" for future use in calculation of relevance scores of the article and a member account having the member account feature "mf1". The second transformation feature thereby represents a pre-computed coefficient that represents a relevance weight of the article for any member account that has the global member feature "mf2" that takes into account that the article features "af1," "af2" of the article will always be co-occurring with each other. The Fast Ranker Engine 206 stores the second transformation feature with an identifier associated with the "mf2" for future use in calculation of relevance scores of the article and a member account having the member account feature "mf1".

By computing the transformation features for the global model member features, the Fast Ranker Engine 206 vastly improves the performance of a computer system be increasing the speed and efficiency of executing scoring by the global model since the pre-computed transformation features eliminate the requirement of assembling vectors for article features—since transformation features already account for co-occurring article features.

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured. circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation, and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partial processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs)).

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 7:
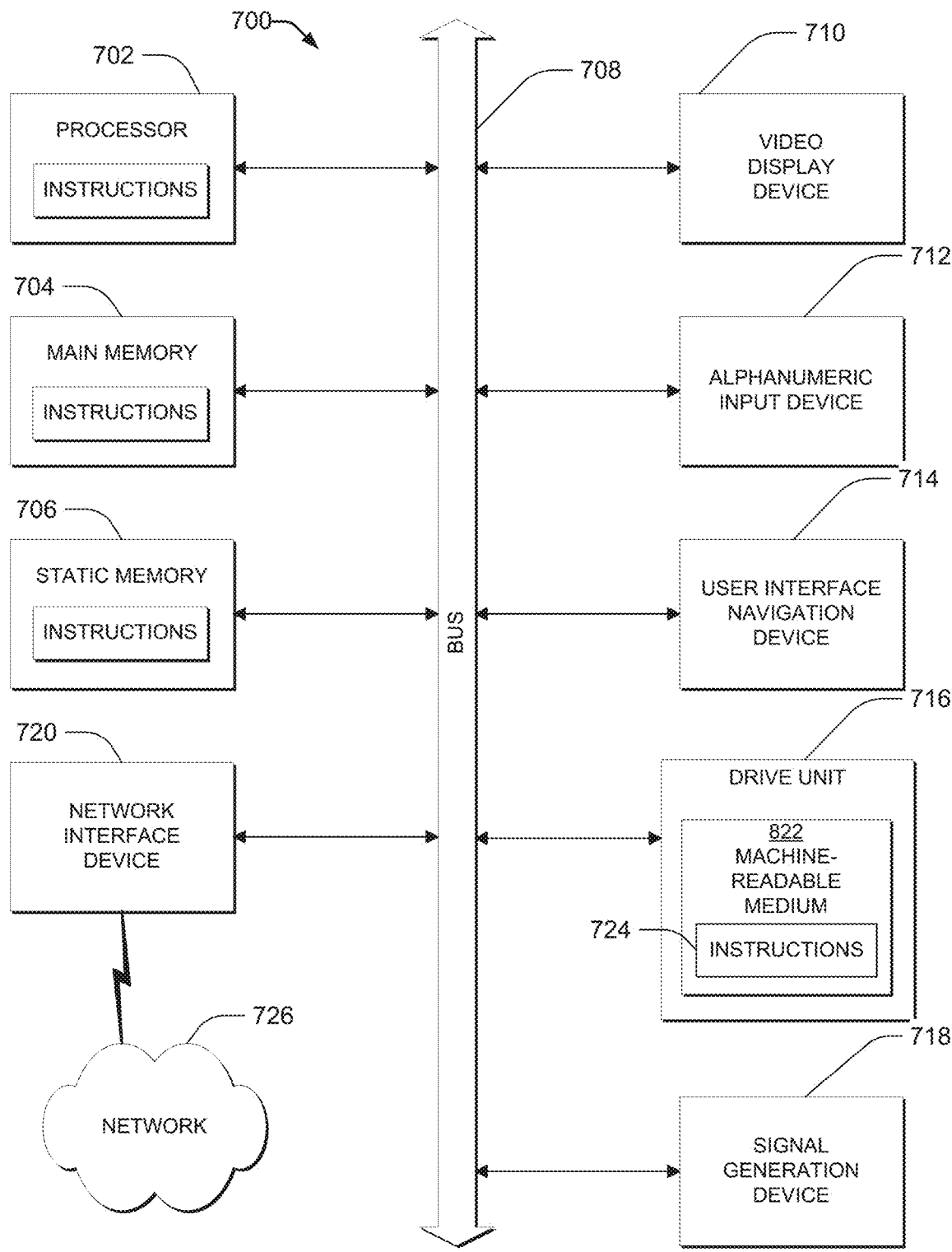
FIG. 7 is a block diagram of an example computer system on which methodologies described herein may be executed, in accordance with an example embodiment.

FIG. 7 is a block diagram of an example computer system 700 on which methodologies described herein may be executed, in accordance with an example embodiment. In alternative embodiments, the machine operates as a stand-alone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 700 includes a processor 702 (e.g., a central processing unit (CPU), a graphics processing unit (GPU) or both), a main memory 704, and a static memory 706, which communicate with each other via a bus 708. Computer system 700 may further include a video display device 710 (e.g., a liquid crystal display (LCD) or a cathode ray tube (CRT)). Computer system 700 also includes an alphanumeric input device 712 (e.g., a keyboard), a user interface (UI) navigation device 714 (e.g., a mouse or touch sensitive display), a disk drive unit 716, a signal generation device 718 (e.g., a speaker) and a network interface device 720.

Disk drive unit 716 includes a machine-readable medium 722 on which is stored one or more sets of instructions and data structures (e.g., software) 724 embodying or utilized by any one or more of the methodologies or functions described herein. Instructions 724 may also reside, completely or at least partially, within main memory 704, within static memory 706, and/or within processor 702 during execution thereof by computer system 700, main memory 704 and processor 702 also constituting machine-readable media.

While machine-readable medium 722 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present technology, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

Instructions 724 may further be transmitted or received over a communications network 726 using a transmission medium. Instructions 724 may be transmitted using network interface device 720 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMAX networks). The term "transmission medium" shall be taken to include any intangible medium that is capable of storing, encoding or carrying instructions for execution by the machine, and includes digital or analog communications signals or other intangible media to facilitate communication of such software.

Although an embodiment has been described with reference to specific example embodiments, it will be evident that various modifications and changes may be made to these embodiments without departing from the broader spirit and scope of the technology. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the terms "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer system, comprising:
   a processor;
   a memory device holding at least one instruction set executable on the processor to cause the computer system to perform operations comprising:
   training a global model having a plurality of global model features, the plurality of global model features including at least one global member feature and at least one global article feature, the global model trained to predict a relevance of an article identified when using the global model to an member identified when using the global model, the training producing a first set of coefficients and second set of coefficients, each coefficient in the first set of coefficients corresponding to a different global member feature and each coefficient in the second set of coefficients corresponding to a different global article feature;
   training a separate prediction model for each article in a plurality of articles, each prediction model having a set of per-article features identified based on profile data of member accounts that have already interacted with the article corresponding to the prediction model;
   identifying global article features present in a first article in a social network service;
   for each of the plurality of global member features, generating a transformation feature for each of a plurality of articles using a coefficient corresponding to the global member feature in the first set of coefficients and using a coefficient corresponding to the global article feature in the second set of coefficients;
   when using the global model, obtaining an identification of a first member and an identification of the first article;
   based upon the identification of the first article and the identification of the first member, retrieving the transformation features for the first article for each global member feature present in the first article; and
   using the global model to predict relevance of the first article to the first member using the retrieved transformation features.

2. The computer system of claim 1, further comprising:
   storing in cache memory the global model and each prediction model of a respective article from a plurality of candidate articles, the global model including at least one global member feature having a corresponding global member feature coefficient and at least one global article feature having a corresponding global article feature coefficient, each prediction model including at least one per-article member feature having a corresponding per-article member coefficient.

3. The computer system of claim 2, wherein each global member feature is based on at least any one of the following types of member account profile data:
   one or more industry descriptors, one or more job title descriptors, one or more employer company descriptors, one or more educational institution descriptors, one or more field of study descriptors, one or more geographic area descriptors and one or more professional level of experience indicators.

4. The computer system of claim 3, wherein each global article feature is based on at least any one of the following types of social network data for one or more articles:
   one or more keywords descriptors, one or more author descriptors, one or more topic descriptors, an article age, presence in one or more member group discussions and an amount of article comments.

5. The computer system of claim 2, wherein identifying global model features present in an article in a social network service comprises:
   identifying presence, in a first article in a plurality of candidate articles, of a plurality of global article features from the global model;
   wherein assembling respective fixed vectors based on at least one member account feature and each coefficient that corresponds to a present global article feature of the global model comprises:
   assembling a fixed member feature vector for each respective global member feature; and
   assembling multiple instances of a fixed coefficient vector based on respective global article feature coefficients that correspond to the plurality of global article features present in the article.

6. The computer system as in claim 5; wherein generating a transformation feature for a prediction model of the article based on the respective fixed vectors comprises:
   for each global member feature, calculating feature transformation data for a respective global member feature and a given instance of the fixed coefficient vector.

7. The computer system as in claim 6, wherein calculating feature transformation data for a respective global member feature and a given instance of the fixed coefficient vector comprises:
   calculating first feature transformation data for a first global member feature and a first instance of the fixed coefficient vector; and
   calculating second feature transformation data for a second global member feature and a second instance of the fixed coefficient vector.

8. The computer system as in claim 7, further comprising:
   generating a first association between the first global member feature in the global model and the first feature transformation data; and
   generating a second association between the second global member feature in the global model and the second feature transformation data.

9. A non-transitory computer-readable medium storing executable instructions thereon, which, when executed by a processor, cause the processor to perform operations including:
   training a global model having a plurality of global model features, the plurality of global model features including at least one global member feature and at least one

17 global article feature, the global model trained to predict a relevance of an article identified when using the global model to an member identified when using the global model, the training producing a first set of coefficients and second set of coefficients, each coefficient in the first set of coefficients corresponding to a different global member feature and each coefficient in the second set of coefficients corresponding to a different global article feature;

training a separate prediction model for each article in a plurality of articles, each prediction model having a set of per-article features identified based on profile data of member accounts that have already interacted with the article corresponding to the prediction model;

identifying global article features present in a first article in a social network service;

for each of the plurality of global member features, generating a transformation feature for each of a plurality of articles using a coefficient corresponding to the global member feature in the first set of coefficients and using a coefficient corresponding to the global article feature in the second set of coefficients;

when using the global model, obtaining an identification of a first member and an identification of the first article;

based upon the identification of the first article and the identification of the first member, retrieving the transformation features for the first article for each global member feature present in the first article; and using the global model to predict relevance of the first article to the first member using the retrieved transformation features.

10. The non-transitory computer-readable medium of claim 9, further comprising:

storing in cache memory the global model and each prediction model of a respective article from a plurality of candidate articles, the global model including at least one global member feature having a corresponding global member feature coefficient and at least one global article feature having a corresponding global article feature coefficient, each prediction model including at least one per-article member feature having a corresponding per-article member coefficient.

11. The non-transitory computer-readable medium of claim 10, wherein each global member feature is based on at least any one of the following types of member account profile data:

one or more industry descriptors, one or more job title descriptors, one or more employer company descriptors, one or more educational institution descriptors, one or more field of study descriptors, one or more geographic area descriptors and one or more professional level of experience indicators.

12. The non-transitory computer-readable medium of claim 11, wherein each global article feature is based on at least any one of the following types of social network data for one or more articles:

one or more keywords descriptors, one or more author descriptors, one or more topic descriptors, an article age, presence in one or more member group discussions and an amount of article comments.

13. The non-transitory computer-readable medium of claim 10, wherein identifying global model features present in an article in a social network service comprises:

identifying presence, in a first article in a plurality of candidate articles, of a plurality of global article features from the global model;

18 wherein assembling respective fixed vectors based on at least one member account feature and each coefficient that corresponds to a present global article feature of the global model comprises:

assembling a fixed member feature vector for each respective global member feature; and assembling multiple instances of a fixed coefficient vector based on respective global article feature coefficients that correspond to the plurality of global article features present in the article.

14. The non-transitory computer-readable medium as in claim 13, wherein generating a transformation feature for a prediction model of the article based on the respective fixed vectors comprises:

for each global member feature, calculating feature transformation data for a respective global member feature and a given instance of the fixed coefficient vector.

15. The non-transitory computer-readable medium as in claim 14, wherein calculating feature transformation data for a respective global member feature and a given instance of the fixed coefficient vector comprises:

calculating first feature transformation data for a first global member feature and a first instance of the fixed coefficient vector; and calculating second feature transformation data for a second global member feature and a second instance of the fixed coefficient vector.

16. The non-transitory computer-readable medium as in claim 15, further generating a first association between the first global member feature in the global model and the first feature transformation data; and generating a second association between the second global member feature in the global model and the second feature transformation data.

17. A method comprising:

training a global model having a plurality of global model features, the plurality of global model features including at least one global member feature and at least one global article feature, the global model trained to predict a relevance of an article identified when using the global model to an member identified when using the global model, the training, producing a first set of coefficients and second set of coefficients, each coefficient in the first set of coefficients corresponding to a different global member feature and each coefficient in the second set of coefficients corresponding to a different global article feature;

training a separate prediction model for each article in a plurality of articles, each prediction model having a set of per-article features identified based on profile data of member accounts that have already interacted with the article corresponding to the prediction model;

identifying global article features present in a first article in a social network service;

for each of the plurality of global member features, generating a transformation feature for each of a plurality of articles using a coefficient corresponding to the global member feature in the first set of coefficients and using a coefficient corresponding to the global article feature in the second set of coefficients;

when using the global model, obtaining an identification of a first member and an identification of the first article;

based upon the identification of the first article and the identification of the first member, retrieving the transformation features for the first article for each global member feature present in the first article; and using the global model to predict relevance of the first article to the first member using the retrieved transformation features.

18. The method of claim 17, further comprising:

storing in cache memory the global model and each prediction model of a respective article from a plurality of candidate articles, the global model including at least one global member feature having a corresponding global member feature coefficient and at least one global article feature having a corresponding global article feature coefficient, each prediction model including at least one per-article member feature having a corresponding per-article member coefficient.

19. The method of claim 18, wherein identifying global model features present in an article in a social network service comprises:

identifying presence, in a first article in a plurality of candidate articles, of a plurality of global article features from the global model;

wherein assembling respective fixed vectors based on at least one member account feature and each coefficient that corresponds to a present global article feature of the global model comprises:

assembling a fixed member feature vector for each respective global member feature; and assembling multiple instances of a fixed coefficient vector based on respective global article feature coefficients that correspond to the plurality of global article features present in the article.

20. The method as in claim 19, wherein generating a transformation feature for a prediction model of the article based on the respective fixed vectors comprises:

for each global member feature, calculating feature transformation data for a respective global member feature and a given instance of the fixed coefficient vector.

* * * * *

UNITED STATES PATENT AND TRADEMARK OFFICE
CERTIFICATE OF CORRECTION

PATENT NO. : 11,205,136 B2
APPLICATION NO. : 15/441967
DATED : December 21, 2021
INVENTOR(S) : Saha et al.

Page 1 of 1

It is certified that error appears in the above-identified patent and that said Letters Patent is hereby corrected as shown below:

In the Claims

In Column 16, Line 38, in Claim 6, delete "claim 5;" and insert --claim 5,-- therefor In Column 18, Line 30, in Claim 16, after "further", insert --comprising:--

In Column 18, Line 44, in Claim 17, delete "training," and insert --training-- therefor Signed and Sealed this
Eighth Day of March, 2022

Drew Hirshfeld
*Performing the Functions and Duties of the
Under Secretary of Commerce for Intellectual Property and
Director of the United States Patent and Trademark Office*